(12) United States Patent
Rana

(10) Patent No.: US 9,410,128 B2
(45) Date of Patent: Aug. 9, 2016

(54) METHOD AND COMPOUNDS FOR GENERATION OF IPSCS

(75) Inventor: Tariq M. Rana, San Diego, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 907 days.

(21) Appl. No.: 13/402,664

(22) Filed: Feb. 22, 2012

(65) Prior Publication Data

US 2012/0213746 A1 Aug. 23, 2012

Related U.S. Application Data

(60) Provisional application No. 61/445,481, filed on Feb. 22, 2011.

(51) Int. Cl.
| | |
|---|---|
| *C12N 5/00* | (2006.01) |
| *C12N 5/06* | (2006.01) |
| *C12N 5/08* | (2006.01) |
| *C07H 21/04* | (2006.01) |
| *C12N 5/074* | (2010.01) |
| *G01N 33/50* | (2006.01) |
| *C07H 21/02* | (2006.01) |

(52) U.S. Cl.
CPC .......... *C12N 5/0696* (2013.01); *G01N 33/5073* (2013.01); *C07H 21/02* (2013.01); *C07H 21/04* (2013.01); *C12N 2310/11* (2013.01); *C12N 2310/14* (2013.01); *C12N 2310/141* (2013.01); *C12N 2501/415* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2501/998* (2013.01); *C12N 2503/02* (2013.01); *C12N 2506/00* (2013.01); *C12N 2506/1307* (2013.01)

(58) Field of Classification Search
CPC .......... C12N 5/0696; C12N 2501/602; C12N 2501/603; C12N 2501/604; C12N 2501/606; C12N 2506/00; C12N 2506/1307; C12N 2310/11; C12N 2310/14; C12N 2310/141; C07H 21/02; C07H 21/04

USPC ......... 435/325, 357, 366, 375, 377; 536/23.5, 536/24.5

See application file for complete search history.

(56) References Cited

U.S. PATENT DOCUMENTS

| | | | |
|---|---|---|---|
| 2009/0047263 | A1 | 2/2009 | Yamanaka et al. |
| 2010/0120142 | A1 | 5/2010 | Impola et al. |
| 2011/0053244 | A1* | 3/2011 | Oyler et al. |
| 2013/0195812 | A1* | 8/2013 | Kikyo et al. |

FOREIGN PATENT DOCUMENTS

| | | |
|---|---|---|
| EP | 2 096 169 A1 | 9/2009 |
| WO | WO 2009/152485 A2 | 12/2009 |
| WO | WO 2010/075575 A1 | 7/2010 |

OTHER PUBLICATIONS

Bellin et al., 2012, Nature reviews/Molecular Cell Biology, vol. 13, p. 713-726.*
Rezanejad et al., 2012, Cellular reprogramming, vol. 14, No. 6, p. 459-470.*
Li et al., 2014, Journal of Hematology & Oncology, 7:50, p. 1-18.*
Bennett, J., 2003, Gene Therapy, vol. 10, p. 977-982.*
Thomas et al., 2003, Nature Reviews/ Genetics, vol. 4, p. 346-358.*
Kodama et al., 2006, Current Medicinal Chemistry, vol. 13, p. 2155-2161.*
Takahashi et al., 2012, Frontiers in Bioscience, vol. S4, p. 133-141.*
Kaur et al., 2009, Current Gene Therapy, vol. 9. p. 434-458.*
Takahashi et al., 2007, Cell, vol. 131, p. 861-872.*
Moriguchi et al., "The generation of human induced pluripotent stem (iPS) cells from liver progenitor cells by only small molecules and the risk for malignant transformations of the cells", *Academic Collaborations for Sick Children*, Oct. 29, 2010, vol. 2, No. 1, pp. 5-9.
International Search Report (ISR) from PCT/US2012/26186.

* cited by examiner

*Primary Examiner* — Shin Lin Chen
(74) *Attorney, Agent, or Firm* — DLA Piper LLP (US)

(57) ABSTRACT

The present invention is based on the seminal concept of combining genomics and chemical biology to identify new agents useful for induced pluripotent stem cell (iPSC) generation. The invention provides a method of generating an iPSC utilizing agents that antagonize a cell specific gene or upregulate expression or activity of a nuclear reprogramming gene, as well as a method of screening for such agents.

12 Claims, 12 Drawing Sheets

A)

1)  Nabumetone

2)  4-Hydroxytamoxifen

3)  Corynanthine hydrochloride

4)  Moclobemide

5) $NiSO_4 \cdot 6H_2O$

6) Lectin

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(10)
<223> OTHER INFORMATION: n is a, c, g, or t

<400> SEQUENCE: 1
ttggcnnnnn gccaa                                                    15

US 9,410,128 B2

METHOD AND COMPOUNDS FOR GENERATION OF IPSCS

CROSS REFERENCE TO RELATED APPLICATION(S)

This application claims the benefit of priority under 35 U.S.C. §119(e) of U.S. Ser. No. 61/445,481, filed Feb. 22, 2011, the entire contents of which is incorporated herein by reference in its entirety.

BACKGROUND

1. Field of the Invention

The invention relates generally to the field of induced pluripotent stem cells (iPSCs) and more specifically to methods of generating such cells, as well as identifying agents useful in generating iPSCs.

2. Background Information

Embryonic stem (ES) cells are not only versatile tools for investigating early developmental events but provide a promising source of tissues potentially useful for regenerative therapies. Recent breakthroughs in generating iPSCs provide alternative means to obtain ES-like cells without destroying embryos by introducing four reprogramming factors (Oct3/4, Sox2, and Klf4/c-Myc or Nanog/Lin28) into somatic cells. iPS cells are known to share numerous traits with ES cells, such as colony morphology, transcriptome, self-renewal ability and pluripotency. Moreover, customized therapeutic applications of iPS cells have been reported. Nonetheless, the molecular basis of reprogramming remains unclear.

Reprogramming is a step-wise process moving from differentiated to ES-like stages, a progression that can be monitored using various cellular markers. The differentiation marker, Thy1, is highly expressed in mouse embryonic fibroblasts (MEFs), and its expression in MEFs decreases within a few days of transduction with Oct3/4, Sox2, Klf4, and c-Myc (denoted here 4F: OSKM). Consequently, expression of the stem cell marker SSEA1 increases, followed by activation of other ES markers, such as endogenous Nanog, Oct3/4, and X reactivation. During this process, iPS cells have been shown to be enriched or selected. Increasing evidence indicates that the four reprogramming factors cooperatively initiate the transition of cell identity from somatic to iPS cells.

These data suggest that signature patterns of gene expression in MEFs constitute a barrier for induced reprogramming and that overcoming this barrier may be a rate-limiting step in the reprogramming process. Despite advances in reprogramming, efficiency of reprogramming remains low and inefficient, thus new approaches are necessary to generate iPSCs.

SUMMARY

The present invention is based on the seminal concept of combining genomics and computational chemical biology to identify new agents useful for iPSC generation. The approach provides an alternative to shot-gun screening and accelerates understanding of molecular mechanisms underlying iPSC induction. The present invention utilizes a methodology to analyze genomics datasets of embryonic fibroblasts (EFs) and embryonic stem (ES) cells to identify genes constituting barriers to iPSC reprogramming. Computational chemical biology combined with genomic analysis is used to identify agents, such as small molecules, involved in reprogramming. Use of agents that down-regulate barrier genes greatly increases reprogramming efficiency.

Accordingly, in one aspect, the invention provides a method of generating an iPSC. The method includes: a) contacting a cell with a nuclear reprogramming factor; and b) contacting the cell of (a) with an agent that antagonizes a cell specific gene or upregulates expression or activity of a nuclear reprogramming gene, thereby generating an iPSC. In various embodiments, the agent increases induction or reprogramming efficiency. In various embodiments the nuclear reprogramming factor is a polynucleotide, polypeptide, or small molecule. In one embodiment, the nuclear reprogramming factor is encoded by a gene contained in a recombinant vector introduced into the cell. In various embodiments, the agent is a polynucleotide, polypeptide, or small molecule, for example, one or more agents selected from those listed in Table 2. In related embodiments, the cell specific gene is a gene listed in Table 1.

In another aspect, the invention provides an iPSC produced by the method of the invention.

In another aspect, the invention provides a population of iPSCs produced by the method of the invention.

In another aspect, the invention provides a cell derived by inducing differentiation of an iPSC produced by the method of the invention.

In another aspect, the invention provides a method of screening for an agent that increases induction or reprogramming efficiency in generating an iPSC. The method includes: a) generating an iPSC by contacting a sample comprising a cell with a nuclear reprogramming factor; b) contacting the sample of (a) with a candidate agent determined to antagonize a cell specific gene or upregulate expression or activity of a nuclear reprogramming gene; and c) comparing reprogramming efficiency in the sample contacted with the candidate agent with that of a control sample, wherein an increase in reprogramming efficiency as compared to the control identifies the candidate agent as an agent that increases reprogramming efficiency in generating an iPSC. In various embodiments, determining that the candidate agent antagonizes a cell specific gene or upregulates expression or activity of a nuclear reprogramming gene is performed by meta-analysis or expression analysis. In one embodiment, the method further includes expression analysis to identify a cell specific gene. In some embodiments, the method includes comparing expression of a gene in a partially or terminally differentiated cell with expression in an embryonic stem cell, wherein an increase in expression of the gene in the partially or terminally differentiated cell as compared to the embryonic stem cell is indicative of a cell specific gene.

In another aspect, the invention provides a method of treating a subject with iPSCs generated by the method of the invention. The method includes obtaining a cell from a subject, inducing the cell into an iPSC using the method described herein, inducing differentiation of the iPSC, and introducing the differentiated cell into the subject, thereby treating the condition.

BRIEF DESCRIPTION OF THE DRAWINGS

FIG. 1A is a heat map representing mRNA microarray analysis of mouse ES cells (MES) and MEFs. FIG. 1B is a plot of mRNA expression of various genes. Error bars represent standard deviations of six independent experiments. FIG. 1C is a plot of GFP+ colony number counted by fluorescence microscopy at day 14~16 after transduction. Error bars represent standard deviations of three independent experiments. * p value <0.05; ** p value <0.005.

FIG. 2A displays the structures of six small molecules used in iPS cell reprogramming. FIG. 2B is a plot of GFP+ colony number identified as described in FIG. 1. Error bars represent standard deviations of three independent experiments. * p value <0.05; ** p value <0.005. FIG. 2C is a plot of GFP+ colony number identified as described in FIG. 1 at day 12~14. Error bars represent standard deviations of six independent experiments. * p value <0.05;  p value <0.005; * p value <0.0005. siNT serves as control.

FIG. 3A is a plot of GFP+ colony number identified as described in FIG. 1 at day 21. Error bars represent standard deviations of two independent experiments. * p value <0.05. FIG. 3B is a plot of GFP+ colony number identified as described in FIG. 1 at day 14. Error bars represent standard deviations of six independent experiments. * p value <0.0005. FIG. 3C is a plot of GFP+ colony number identified as described in FIG. 1 at day 15~21. Error bars represent standard deviations of four independent experiments.  p value <0.005. FIG. 3D is a plot of GFP+ colony number identified as described in FIG. 1 at day 17~21. Error bars represent standard deviations of three independent experiments. ** p value <0.005. FIG. 3E is a plot of Sox2 mRNA expression. β actin expression serves as an internal control. Error bars represent standard deviation of 2~3 independent experiments. * p value <0.05.

FIG. 5A is a series of graphs of analysis of real-time qRT-PCR analysis of a selected set of genes during reprogramming. Oct4-MEFs were transduced with OSKM to induce reprogramming. Transduced cells were collected at various time points for isolating total RNAs and real-time qRT-PCR analysis. GAPDH mRNA expression level served as internal control. Expression level of target genes was normalized to those in MEFs. MES served as control. Error bars represent standard deviations of at least two independent experiments. FIG. 5B is a series of graphs of analysis of experiments performed as described in FIG. 5A and which served as indicators of reprogramming progress. Error bars represent standard deviations of at least two independent experiments. FIG. 5C is a series of graphs of analysis of data generated as described in FIG. 5A and which served as indicators of de-differentiation progress. Error bars represent standard deviations of at least two independent experiments. FIG. 5D is a graph of analysis of data generated as described in FIG. 5A. Error bars represent standard deviations of at least two independent experiments.

FIG. 6A is a graph plotting GFP+ colony number of Oct4-MEFs transduced with OSKM to induce reprogramming. Small molecules were applied at day 4~5 post transduction. EGFP+ colony number was scored under fluorescent microscopy at two weeks post transduction. Error bars represent standard deviations of at least three independent experiments. * P value <0.05; ** P value <0.005. FIG. 6B is a graph plotting GFP+ colony number of Oct4-MEFs transduced with OSK to induce reprogramming. Small molecules were applied at day 4~5 post transduction. EGFP+ colony number was scored under fluorescent microscopy at two weeks post transduction. Error bars represent standard deviations of at least three independent experiments. * P value <0.05; ** P value <0.005.

DETAILED DESCRIPTION

The present invention utilizes a methodology of systematic analysis of genomics datasets to identify genomic barriers to iPSC reprogramming. The data presented herein show that combining computational drug screening with genomic analysis allows the identification and use of agents, such as small molecules, that regulate reprogramming, to increase reprogramming efficiency.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Figure 1:
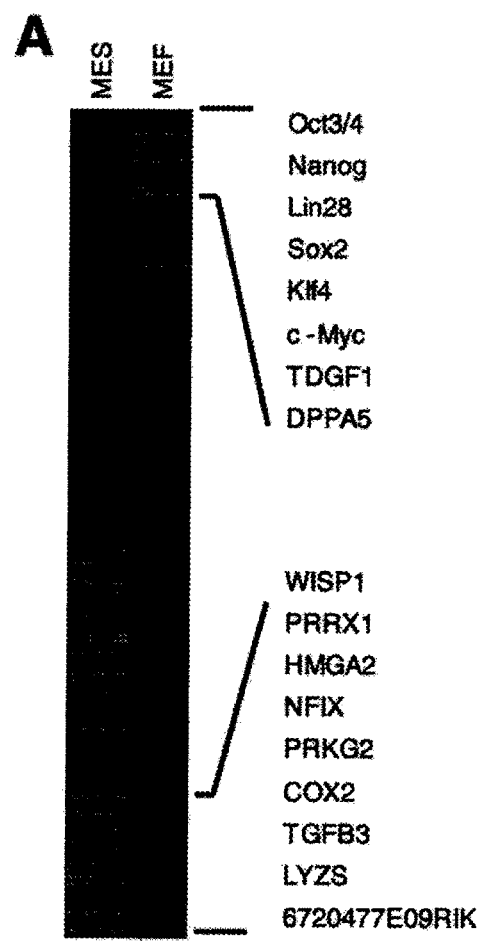
FIG. 1 is a series of graphical representations.
Figure 1:
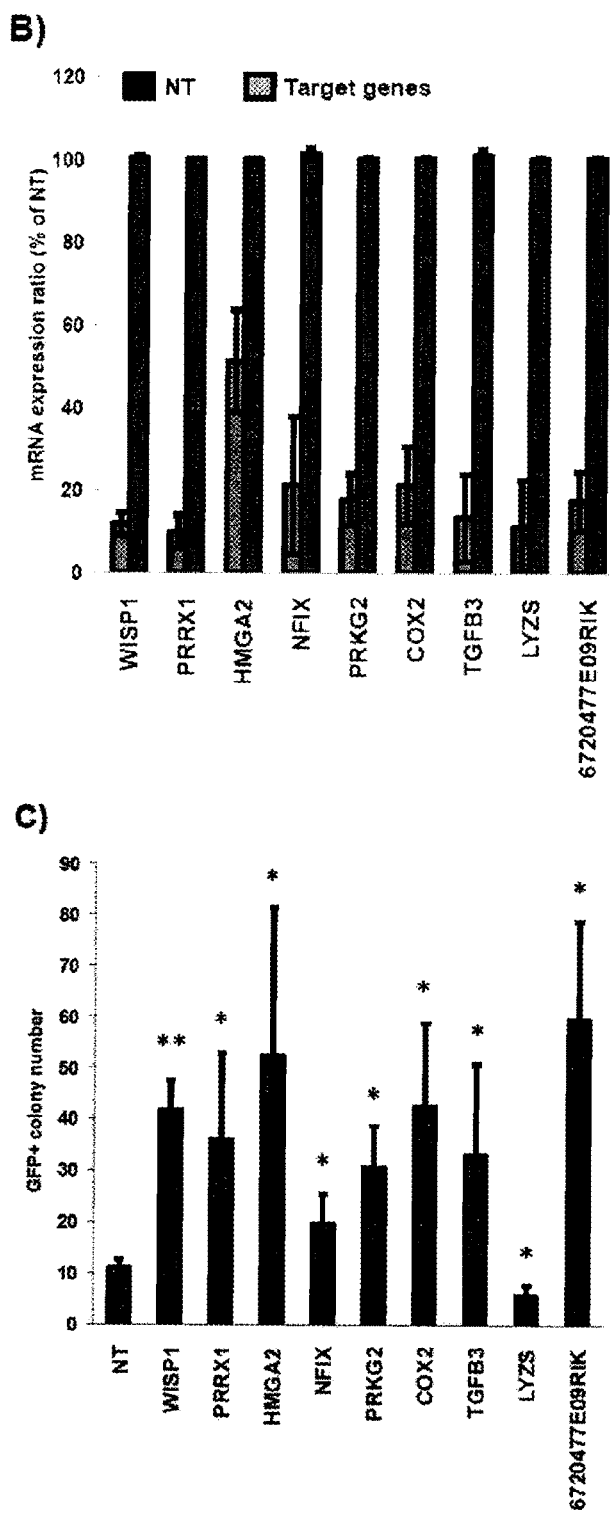
Figure 2:
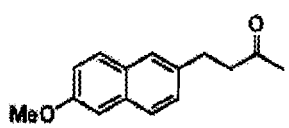
FIG. 2 is a series of graphical representations.
Figure 2:
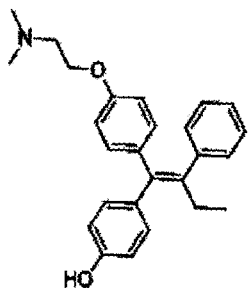
Figure 2:
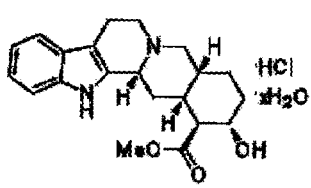
Figure 2:
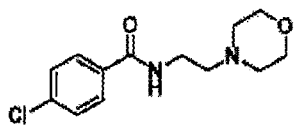
Figure 2:
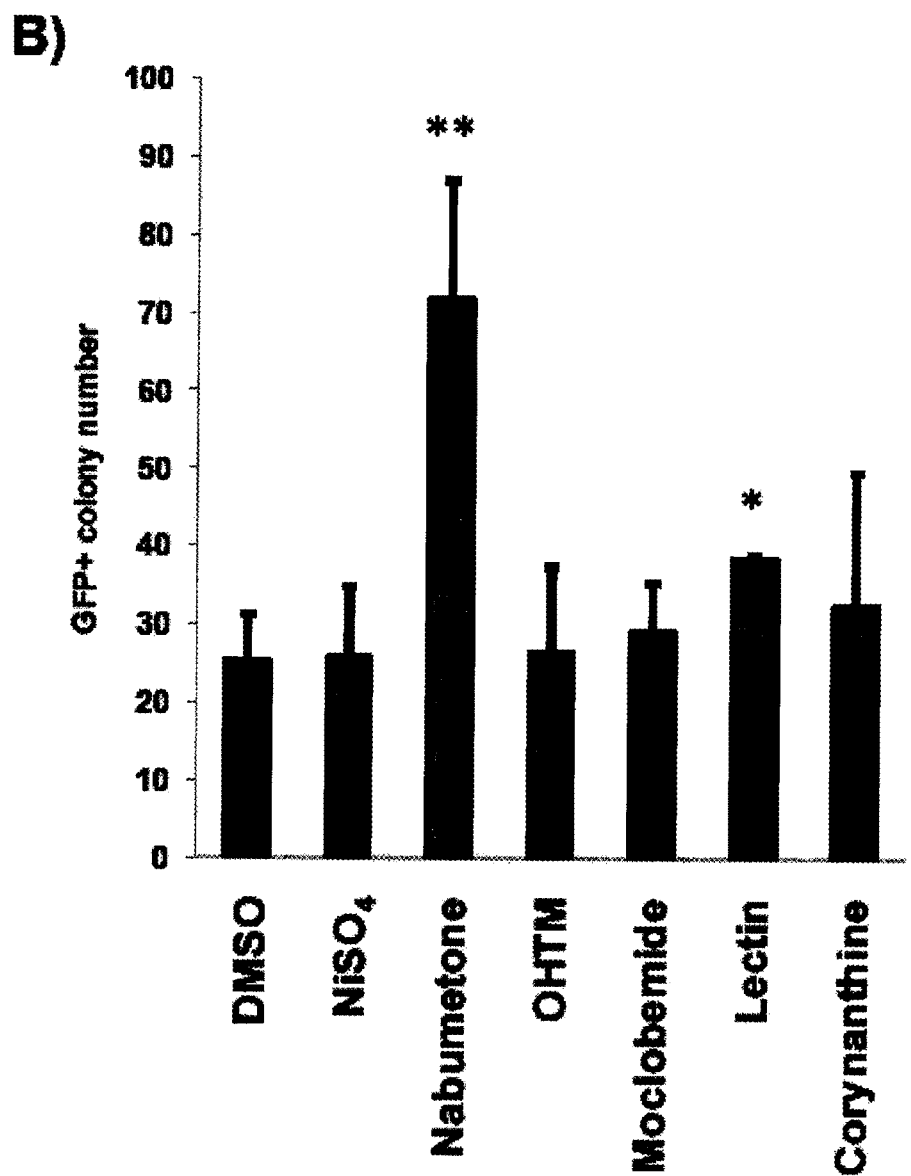
Figure 2:
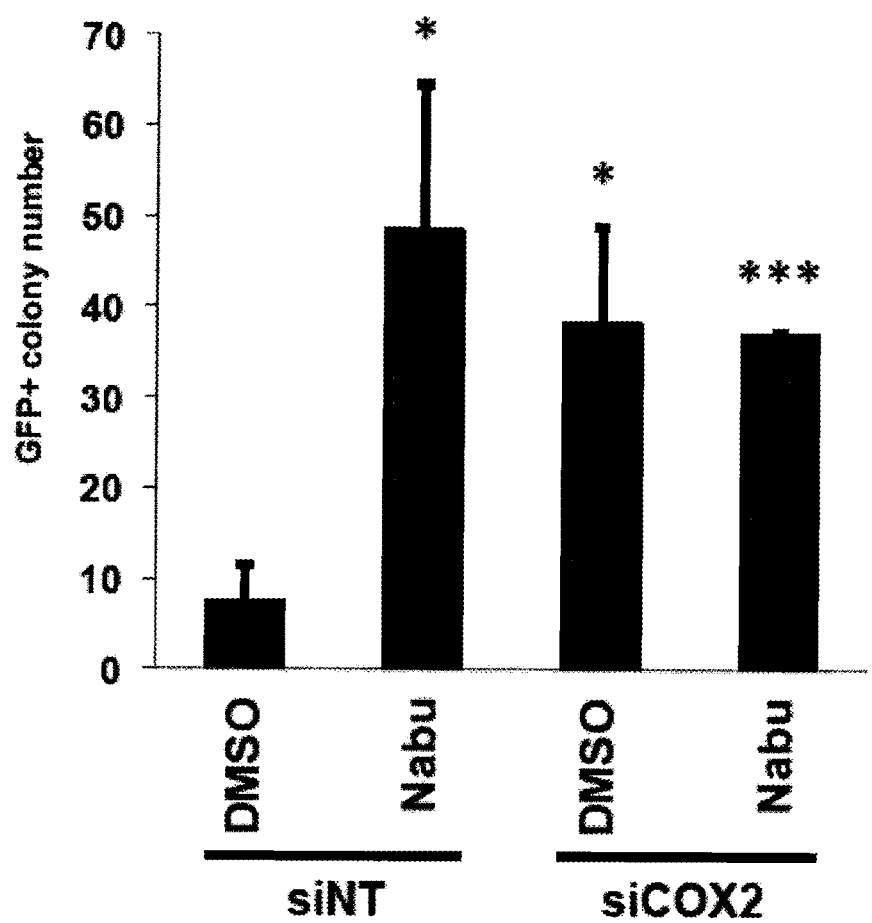
Figure 3:
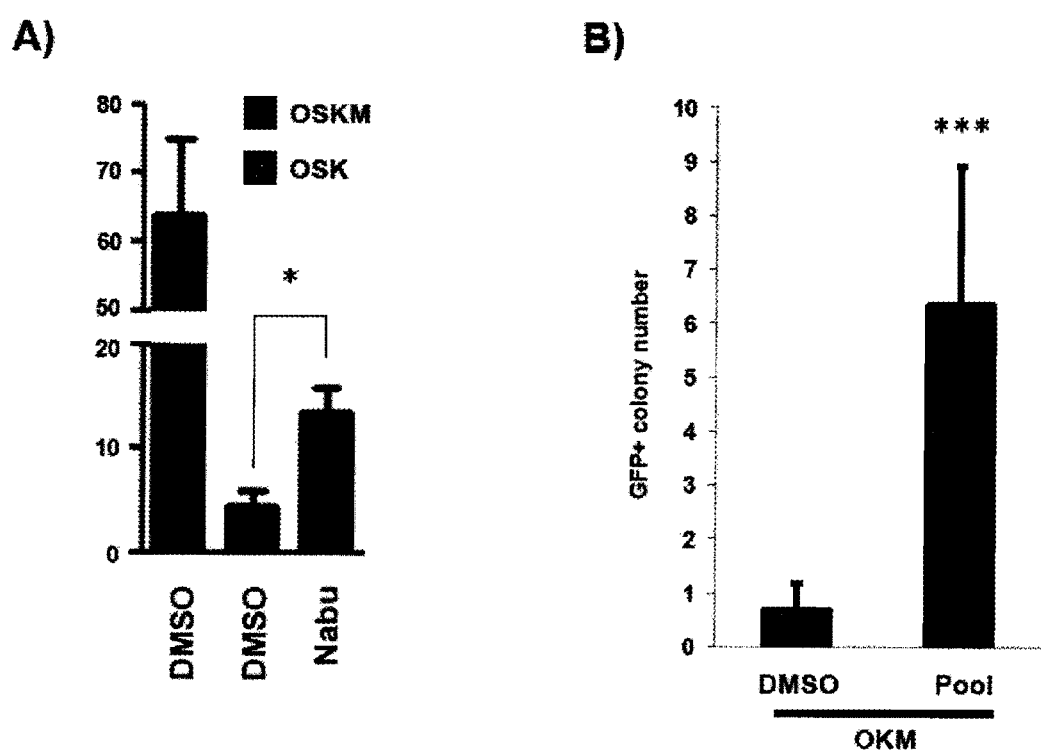
FIG. 3 is a series of graphical representation.
Figure 3:
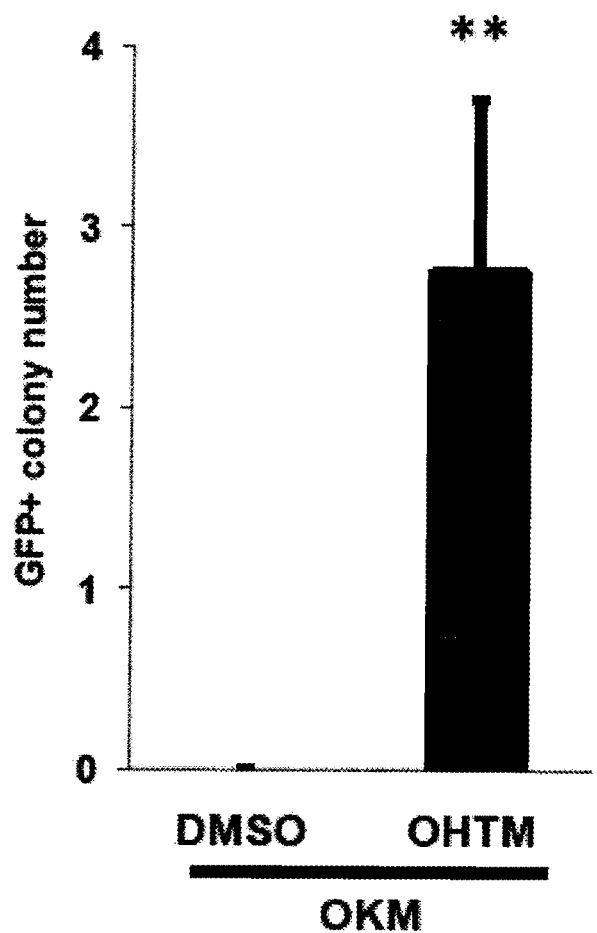
Figure 3:
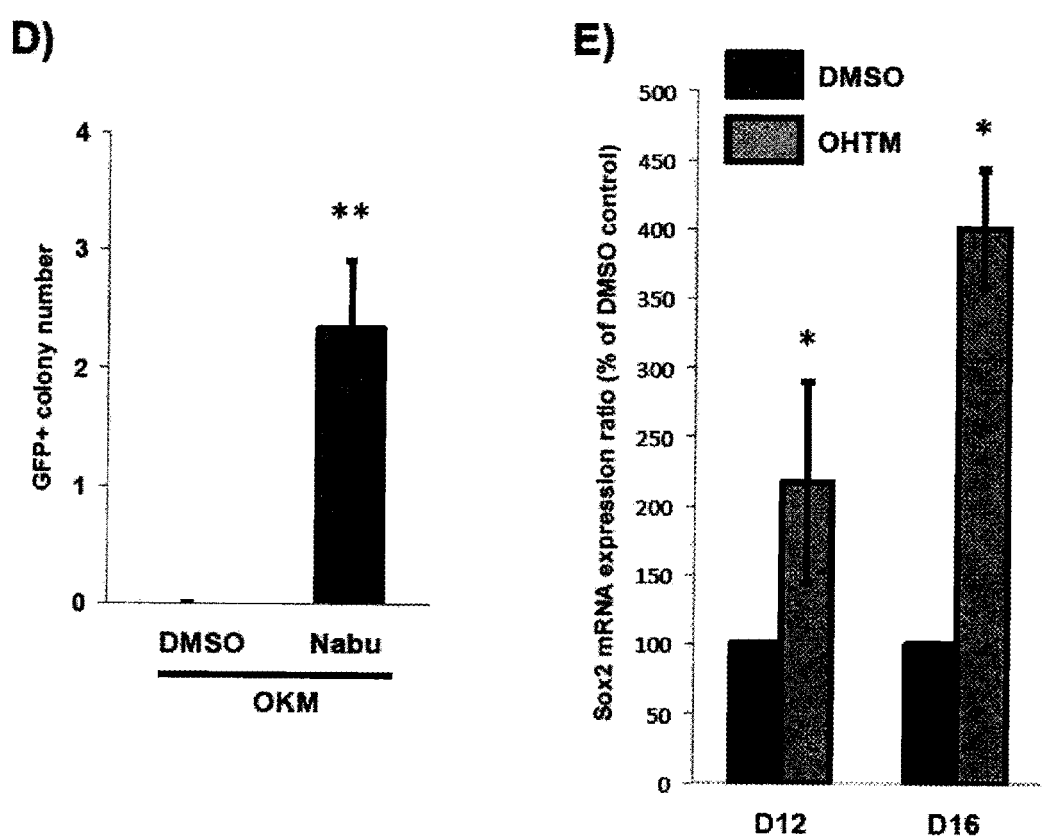

As discussed herein, the methodology of the present invention is based on the premise that reprogramming somatic cells requires overcoming networks specific to somatic cells, as opposed to embryonic stem cells. It was observed that specific siRNA-mediated knockdown in somatic cells, mouse embryonic fibroblasts (MEFs), of genes encoding catalytic or regulatory proteins, such as WISP1, PRRX1, HMGA2, NFIX, PRKG2, COX2, 6720477E09RIK, and TGFβ3, significantly enhanced reprogramming (FIG. 1). To accelerate screening of small molecules, a computational screening method was employed using a data-mining framework to identify agents (FIG. 2), including nabumetone, 4-hydroxytamoxifen (OHTM), corynanthine, moclobemide, nickel sulfate hexahydrate ($NiSO_4$), and lectin, which function to reprogram somatic cells without use of nuclear reprogramming genes, such as Sox2 (FIG. 3). For example OHTM, was found to partially replace the Sox2 transgene during reprogramming by inducing endogenous Sox2 expression (FIG. 3). It was further shown that nabumetone enhances reprogramming by inhibiting COX2 activity (FIG. 3) and promotes reprogramming by supplementing c-Myc or Sox2 function without compromising self-renewal and pluripotency of small molecule-derived iPSCs.

Accordingly, in one aspect, the invention provides a method of generating an iPSC. The method includes: a) contacting a cell with a nuclear reprogramming factor; and b) contacting the cell of (a) with an agent that antagonizes a cell specific gene or upregulates expression or activity of a nuclear reprogramming gene, thereby generating an iPSC.

In another aspect, the invention provides a method of screening for an agent that increases induction or reprogramming efficiency in generating an iPSC. The method includes: a) generating an iPSC by contacting a sample comprising a cell with a nuclear reprogramming factor; b) contacting the sample of (a) with a candidate agent determined to antagonize a cell specific gene or upregulate expression or activity of a nuclear reprogramming gene; and c) comparing reprogramming efficiency in the sample contacted with the candidate agent with that of a control sample, wherein an increase in reprogramming efficiency as compared to the control identifies the candidate agent as an agent that increases reprogramming efficiency in generating an iPSC.

In various embodiments, one or more nuclear reprogramming factors are used to induce reprogramming of a differentiated cell, such as a somatic cell, without using eggs, embryos, or ES cells. Efficiency of the induction process is enhanced by utilizing an agent that antagonizes a cell specific gene or upregulates expression or activity of a nuclear reprogramming gene during the induction process. The method may be used to conveniently and highly reproducibly establish an iPSC having pluripotency and growth ability similar to those of ES cells. For example, the nuclear reprogramming factor may be introduced into a cell by transducing the cell with a recombinant vector comprising a gene encoding the nuclear reprogramming factor along with along with the agent. Accordingly, the cell can express the nuclear reprogramming factor expressed as a product of a gene contained in the recombinant vector. The agent acts to antagonize a cell specific gene or upregulate expression or activity of a nuclear reprogramming gene during the induction process to induce reprogramming of a differentiated cell at an increased efficiency rate as compare to use of the nuclear reprogramming factor alone. The agent may also substitute for a specific nuclear reprogramming factor, for example, Sox2. Generation of iPSCs utilizing the method described herein provides for an ideal platform for screening for new agents that act as nuclear reprogramming factors or work synergistically to increase induction efficiency.

As used herein, pluripotent cells include cells that have the potential to divide in vitro for an extended period of time (greater than one year) and have the unique ability to differentiate into cells derived from all three embryonic germ layers, including the endoderm, mesoderm and ectoderm.

Somatic cells for use with the present invention may be primary cells or immortalized cells. Such cells may be primary cells (non-immortalized cells), such as those freshly isolated from an animal, or may be derived from a cell line (immortalized cells). In an exemplary aspect, the somatic cells are mammalian cells, such as, for example, human cells or mouse cells. They may be obtained by well-known methods, from different organs, such as, but not limited to skin, lung, pancreas, liver, stomach, intestine, heart, reproductive organs, bladder, kidney, urethra and other urinary organs, or generally from any organ or tissue containing living somatic cells. Mammalian somatic cells useful in the present invention include, by way of example, adult stem cells, sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other known muscle cells, and generally any live somatic cells. In particular embodiments, fibroblasts are used. The term somatic cell, as used herein, is also intended to include adult stem cells. An adult stem cell is a cell that is capable of giving rise to all cell types of a particular tissue. Adult stem cells include cells such as, hematopoietic stem cells, neural stem cells, and mesenchymal stem cells.

Additional cells for use include partially or terminally differentiated cells, such as, but not limited to multipotent, oligopotent or unipotent cells, progenitor cells and somatic cells.

As used herein, the term "sample" refers to any sample suitable for the method provided by the present invention. For example, a sample can be any sample that includes a somatic cell, including, for example, a bodily fluid; a tissue; or a sample of an organ. A sample, for example, from a human subject, can be obtained using well known and routine clinical methods (e.g., a biopsy procedure)

As used herein, reprogramming, is intended to refer to a process that alters or reverses the differentiation status of a somatic cell that is either partially or terminally differentiated. Reprogramming of a somatic cell may be a partial or complete reversion of the differentiation status of the somatic cell. In an exemplary aspect, reprogramming is complete wherein a somatic cell is reprogrammed into an iPSC. However, reprogramming may be partial, such as reversion into any less differentiated state. For example, reverting a terminally differentiated cell into a cell of a less differentiated state, such as a multipotent cell.

In various embodiments of the present invention, nuclear reprogramming factors are genes, such as nuclear reprogramming genes, that induce pluripotency and are utilized to reprogram differentiated or semi-differentiated cells to a phenotype that is more primitive than that of the initial cell, such as the phenotype of a PSC. Such genes are utilized with agents determined to antagonize a somatic cell specific gene or upregulate expression or activity of a nuclear reprogramming gene to increase induction efficiency. Such genes and agents are capable of generating a PSC from a somatic cell upon expression of one or more such genes having been integrated into the genome of the somatic cell. As used herein, a gene that induces pluripotency is intended to refer to a gene that is associated with pluripotency and capable of generating a less differentiated cell, such as a PSC from a somatic cell upon integration and expression of the gene. The expression of a pluripotency gene is typically restricted to PSCs, and is crucial for the functional identity of PSCs.

In various embodiments, the present invention utilizes an agent that antagonizes or inhibits expression of a cell specific gene (or product thereof) or upregulates expression or activity of a nuclear reprogramming gene. One of skill in the art would appreciate that agents capable of antagonizing a cell specific gene or upregulating expression or activity of a nuclear reprogramming gene can include a variety of different types of molecules. An agent or candidate agent useful in any method of the invention can be any type of molecule, for example, a polynucleotide, a peptide, a peptidomimetic, peptoids such as vinylogous peptoids, chemical compounds, such as organic molecules or small organic molecules, or the like. In one embodiment, an agent or candidate agent for use in the method of the present invention is a polynucleotide, such as an antisense oligonucleotide or RNA molecule. In various embodiments, the agent or candidate agent may be a polynucleotide, such as an antisense oligonucleotide or RNA molecule, such as microRNA, dsRNA, siRNA, stRNA, and shRNA. In various aspects, the agent is selected from those listed in Table 2.

As used herein, a "cell specific gene" or "somatic cells specific gene" includes genes which are expressed in higher levels in partially or terminally differentiated cells or cell types as compared to their expression in an embryonic or PSC. Various techniques for determining and comparing gene expression levels in cells are known in the art that may be suitable for use with the present invention, including but no limited to gene chip analysis, protein activity level and the like. In various embodiments, a cell specific gene includes a gene whose expression in somatic cells is at least 10, 20, 30, 40, 50, 60, 70, 80, 90, 100, 150 or 200% or greater as compared to expression in an ES cell. For example, a cell specific gene may be any gene listed in Table 1.

Identifying an agent as being capable of antagonizing a cell specific gene or upregulating expression or activity of a nuclear reprogramming gene may be performed by a number of methods known in the art. For example, identification may include meta-analysis which generally entails data mining and interrogation of various curated databases to determine proposed or known biological activity of an agent. One such meta-analysis method for use in the present invention utilizes NextBio (nextbio.com) data-mining tools to collect information from public data sources as described in Kupershmidt et al. (*PLoS* One 5 (2010); incorporated herein by reference in entirety).

Polynucleotides of the present invention, such as antisense oligonucleotides and RNA molecules may be of any suitable length. For example, one of skill in the art would understand what length are suitable for antisense oligonucleotides or RNA molecule to be used to regulate gene expression. Such molecules are typically from about 5 to 100, 5 to 50, 5 to 45, 5 to 40, 5 to 35, 5 to 30, 5 to 25, 5 to 20, or 10 to 20 nucleotides in length. For example the molecule may be about 5, 10, 15, 16, 17, 18, 19, 20, 21, 22, 23, 24, 25, 26, 27, 28, 29, 30, 31, 32, 33, 34, 35, 40, 45 or 50 nucleotides in length. Such polynucleotides may include from at least about 15 to more than about 120 nucleotides, including at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 110 nucleotides, at least about 120 nucleotides or greater than 120 nucleotides.

The term "polynucleotide" or "nucleotide sequence" or "nucleic acid molecule" is used broadly herein to mean a sequence of two or more deoxyribonucleotides or ribonucleotides that are linked together by a phosphodiester bond. As such, the terms include RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the terms as used herein include naturally occurring nucleic acid molecules, which can be isolated from a cell, as well as synthetic polynucleotides, which can be prepared, for example, by methods of chemical synthesis or by enzymatic methods such as by the polymerase chain reaction (PCR). It should be recognized that the different terms are used only for convenience of discussion so as to distinguish, for example, different components of a composition.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. Depending on the use, however, a polynucleotide also can contain nucleotide analogs, including non-naturally occurring synthetic nucleotides or modified naturally occurring nucleotides. Nucleotide analogs are well known in the art and commercially available, as are polynucleotides containing such nucleotide analogs. The covalent bond linking the nucleotides of a polynucleotide generally is a phosphodiester bond. However, depending on the purpose for which the polynucleotide is to be used, the covalent bond also can be any of numerous other bonds, including a thiodiester bond, a phosphorothioate bond, a peptide-like bond or any other bond known to those in the art as useful for linking nucleotides to produce synthetic polynucleotides.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

In various embodiments antisense oligonucleotides or RNA molecules include oligonucleotides containing modifications. A variety of modification are known in the art and contemplated for use in the present invention. For example oligonucleotides containing modified backbones or non-natural internucleoside linkages are contemplated. As used herein, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In various aspects modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Certain oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

In various aspects modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In various aspects, oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. In various aspects, oligonucleotides may include phosphorothioate backbones and oligonucleosides with heteroatom backbones. Modified oligonucleotides may also contain one or more substituted sugar moieties. In some embodiments oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$ and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, N3, $NH_2$, heterocycloalkyl, heterocycloalkaryl, amino alkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another modification includes 2'-methoxyethoxy($2'OCH_2CH_2OCH_3$, also known as 2'-O-(2-methoxyethyl) or 2'-MOE).

In related aspects, the present invention includes use of Locked Nucleic Acids (LNAs) to generate antisense nucleic acids having enhanced affinity and specificity for the target polynucleotide. LNAs are nucleic acid in which the 2'-hydroxyl group is linked to the 3' or 4' carbon atom of the sugar ring thereby forming a bicyclic sugar moiety. The linkage is preferably a methelyne ($—CH_2—)_n$ group bridging the 2' oxygen atom and the 4' carbon atom wherein n is 1 or 2.

Other modifications include 2'-methoxy(2'-O—$CH_3$), 2'-aminopropoxy(2'-$OCH_2CH_2CH_2NH_2$), 2'-allyl (2'-CH—CH—$CH_2$), 2'-O-allyl (2'-O—$CH_2$—$CHCH_2$), 2'-fluoro (2'-F), 2'-amino, 2'-thio, 2'-Omethyl, 2'-methoxymethyl, 2'-propyl, and the like. The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazi-n-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrimido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases are known in the art, Certain of these nucleobases are particularly useful for increasing the binding affinity of the oligomeric compounds described herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 C and are presently preferred base substitutions, even more particularly when combined with 2'-O-methoxyethyl sugar modifications.

Another modification of the antisense oligonucleotides described herein involves chemically linking to the oligonucleotide one or more moieties or conjugates which enhance the activity, cellular distribution or cellular uptake of the oligonucleotide. The antisense oligonucleotides can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., dihexadecyl-rac-glycerol or triethylammonium 1,2-di-O- hexadecyl-rac-glycero-3-H-phosphonate, a polyamine or a polyethylene glycol chain, or adamantane acetic acid, a palmityl moiety, or an octadecylamine or hexylaminocarbonyloxycholesterol moiety.

Several genes have been found to be associated with pluripotency and may be considered nuclear reprogramming genes or factors and thus suitable for use with the present invention. Such genes are known in the art and include, by way of example, a gene listed in Table 2, SOX family genes (SOX1, SOX2, SOX3, SOX15, SOX18), KLF family genes (KLF1, KLF2, KLF4, KLF5), MYC family genes (C-MYC, L-MYC, N-MYC), SALL4, OCT4, NANOG, LIN28, STELLA, NOBOX or a STAT family gene. STAT family members may include for example STAT1, STAT2, STAT3, STAT4, STAT5 (STAT5A and STAT5B), and STAT6. While in some instances, use of only one gene to induce pluripotency may be possible, in general, expression of more than one gene is required to induce pluripotency. The number of required pluripotency genes is also expected to depend on the agent or agents that are utilized in combination with the nuclear reprogramming gene, since certain agent have been determined to substitute for reprogramming genes. For example, Sox2 may be replaced with OHTM and/or nabumetone. As such, one, two, three, four or more genes may be simultaneously integrated into the somatic cell genome as a polycistronic construct to allow simultaneous expression of such genes. In an one embodiment, up to four genes are utilized to induce pluripotency including any combination of OCT3/4, Sox2, Klf4 and c-MYC. Additional genes known as reprogramming factors suitable for use with the present invention are disclosed in U.S. patent application Ser. No. 10/997,146 and U.S. patent application Ser. No. 12/289,873, incorporated herein by reference.

All of these genes commonly exist in mammals, including human, and thus homologues from any mammals may be used in the present invention, such as genes derived from mammals including, but not limited to mouse, rat, bovine, ovine, horse, and ape. Further, in addition to wild-type gene products, mutant gene products including substitution, insertion, and/or deletion of several (e.g., 1 to 10, 1 to 6, 1 to 4, 1 to 3, and 1 or 2) amino acids and having similar function to that of the wild-type gene products can also be used. Furthermore, the combinations of factors are not limited to the use of wild-type genes or gene products. For example, Myc chimeras or other Myc variants can be used instead of wild-type Myc.

The present invention is not limited to any particular combination of nuclear reprogramming genes or factors. As discussed herein a nuclear reprogramming factor may comprise one or more gene products. The nuclear reprogramming factor may also comprise a combination of gene products as discussed herein. Each nuclear reprogramming factor may be used alone or in combination with other nuclear reprogramming factors as disclosed herein. Further, nuclear reprogramming factors of the present invention can be identified by screening methods, for example, as discussed in U.S. patent application Ser. No. 10/997,146, incorporated herein by reference. Additionally, the nuclear reprogramming factor of the present invention may contain one or more factors relating to differentiation, development, proliferation or the like and factors having other physiological activities, as well as other gene products which can function as a nuclear reprogramming factor.

The nuclear reprogramming factor may comprise a protein or peptide. The protein may be produced from a gene as discussed herein, or alternatively, in the form of a fusion gene product of the protein with another protein, peptide or the like. The protein or peptide may be a fluorescent protein and/or a fusion protein. For example, a fusion protein with green fluorescence protein (GFP) or a fusion gene product with a peptide such as a histidine tag can also be used. Further, by preparing and using a fusion protein with the TAT peptide derived from the virus HIV, intracellular uptake of the nuclear reprogramming factor through cell membranes can be promoted, thereby enabling induction of reprogramming only by adding the fusion protein to a medium thus avoiding complicated operations such as gene transduction. Since preparation methods of such fusion gene products are well known to those skilled in the art, skilled artisans can easily design and prepare an appropriate fusion gene product depending on the purpose.

As discussed herein, an iPSC may be induced by contacting a cell with a nuclear reprogramming factor in combination with an agent that antagonizes a cell specific gene or upregulates expression or activity of a nuclear reprogramming gene. As would be appreciated by one of skill in the art, delivery to the somatic cell may be performed by any suitable method known in the art. In one embodiment, the nuclear reprogramming factor may be introduced into a cell with a recombinant vector comprising a gene encoding the nuclear reprogramming factor.

Recombinant vectors may be introduced into a cell using a variety of well known techniques, such as non-viral based transfection of the cell. In an exemplary aspect the construct is incorporated into a vector and introduced into the cell to allow expression of the construct. Introduction into the cell may be performed by any viral or non-viral based transfection known in the art, such as, but not limited to electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include proprietary transfection reagents such as Lipofectamine™, Dojindo Hilymax™, Fugene™, jetPEI™, Effectene™ and DreamFect™.

Use of a nuclear reprogramming factor in combination with an agent that antagonizes a somatic cell specific gene or upregulates expression or activity of a nuclear reprogramming gene increase the induction efficiency as compared to use of a reprogramming factor alone. In various embodiments, induction efficiency may be increased by 10, 20, 30, 40, 50, 60, 70, 80, 90, 100, 150, 200, 300, 400 or even 500% as compared with convention methods. For example, induction efficiency may be as high as 1, 2, 3, 4, 5, 6, 7, 8, 9, 10, 15, 20, 25 or 50% (e.g., percent of induced cells as compared with total number of starting somatic cells).

During the induction process, the cell may be contacted with the nuclear reprogramming factor simultaneously or before the cell is contact with an agent or candidate agent. In various embodiments, the somatic cell is contacted with the reprogramming factor about 1, 2, 3, 4, 5, 7, 8, 9, 10, 11, 12, 13, 14 or more days before the cell is contacted with any other agent. In some embodiments, the somatic cell is contacted with the reprogramming factor about 1, 2, 3, 4 or 5 days before the cell is contacted with any other agent or inhibitor.

As used herein, "agent" and "candidate agent" are used interchangeably and refer to agents that are known to, or are being investigated for their ability to antagonize a somatic cell specific gene or upregulate expression or activity of a nuclear reprogramming gene.

Further analysis may be performed to assess the pluripotency characteristics of a reprogrammed cell. The cells may be analyzed for different growth characteristics and embryonic stem cell like morphology. For example, cells may be differentiated in vitro by adding certain growth factors known to drive differentiation into specific cell types. Reprogrammed cells capable of forming only a few cell types of the body are multipotent, while reprogrammed cells capable of forming any cell type of the body are pluripotent.

Expression profiling of reprogrammed somatic cells to assess their pluripotency characteristics may also be conducted. Expression of individual genes associated with pluripotency may also be examined. Additionally, expression of embryonic stem cell surface markers may be analyzed. Detection and analysis of a variety of genes known in the art to be associated with PSCs may include analysis of genes such as, but not limited to those listed in Table 2, OCT4, NANOG, SALL4, SSEA-1, SSEA-3, SSEA-4, TRA-1-60, TRA-1-81, or a combination thereof. iPS cells may express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; .beta.III-tubulin; α-smooth muscle actin (α-SMA); fibroblast growth factor 4 (Fgf4), Cripto, Dax1; zinc finger protein 296 (Zfp296); N-acetyltransferase-1 (Nat1); ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthll7; Sall4; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tell); DPPA3/Stella; DPPA4; as well as other general markers for Pluripotency, for example any genes used during induction to reprogram the cell. iPS cells can also be characterized by the down-regulation of markers characteristic of the differentiated cell from which the iPSC is induced.

The invention further provides iPSCs produced using the methods described herein, as well as populations of such cells. The reprogrammed cells of the present invention, capable of differentiation into a variety of cell types, have a variety of applications and therapeutic uses. The basic properties of stem cells, the capability to infinitely self-renew and the ability to differentiate into every cell type in the body make them ideal for therapeutic uses.

Accordingly, in one aspect the present invention further provides a method of treatment or prevention of a disorder and/or condition in a subject using iPSCs generated using the methods described herein. The method includes obtaining a cell from a subject and reprogramming the cell into an iPSC using the methods described herein. The cell is then cultured under suitable conditions to differentiate the cell into a desired cell type suitable for treating the condition. The differentiated cell may then be introducing into the subject to treat or prevent the condition.

In one aspect, the iPS cells produced using the methods described herein, as well as populations of such cells may be differentiated in vitro by treating or contacting the cells with differentiation agents. Such treatment may be used in combination with growth factors or other agents and stimuli commonly known in the art to drive differentiation into specific cell types.

One advantage of the present invention is that it provides an essentially limitless supply of isogenic or synegenic human cells suitable for transplantation. The iPSCs are tailored specifically to the patient, avoiding immune rejection. Therefore, it will obviate the significant problem associated with current transplantation methods, such as, rejection of the transplanted tissue which may occur because of host versus graft or graft versus host rejection. Several kinds of iPSCs or fully differentiated somatic cells prepared from iPS cells from somatic cells derived from healthy humans can be stored in an iPSC bank as a library of cells, and one kind or more kinds of the iPSCs in the library can be used for preparation of somatic cells, tissues, or organs that are free of rejection by a patient to be subjected to stem cell therapy.

The iPSCs of the present invention may be differentiated into a number of different cell types to treat a variety of disorders by methods known in the art. For example, iPSCs may be induced to differentiate into progenitor cells, multipotent cells, oligopotent cells, unipotent cells, hematopoetic stem cells, muscle cells, cardiac muscle cells, liver cells, cartilage cells, epithelial cells, urinary tract cells, neuronal cells, and the like. The differentiated cells may then be transplanted back into the patient's body to prevent or treat a condition. Thus, the methods of the present invention may be used to treat a subject having a myocardial infarction, congestive heart failure, stroke, ischemia, peripheral vascular disease, alcoholic liver disease, cirrhosis, Parkinson's disease, Alzheimer's disease, diabetes, cancer, arthritis, wound healing, immunodeficiency, aplastic anemia, anemia, Huntington's disease, amyotrophic lateral sclerosis (ALS), lysosomal storage diseases, multiple sclerosis, spinal cord injuries, genetic disorders, and similar diseases, where an increase or replacement of a particular cell type/tissue or cellular de-differentiation is desirable.

In various embodiments, the method increases the number of cells of the tissue or organ by at least about 5%, 10%, 25%, 50%, 75% or more compared to a corresponding untreated control tissue or organ. In yet another embodiment, the method increases the biological activity of the tissue or organ by at least about 5%, 10%, 25%, 50%, 75% or more compared to a corresponding untreated control tissue or organ. In yet another embodiment, the method increases blood vessel formation in the tissue or organ by at least about 5%, 10%, 25%, 50%, 75% or more compared to a corresponding untreated control tissue or organ. In yet another embodiment, the cell is administered directly to a subject at a site where an increase in cell number is desired.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Use of Agents in iPSC Induction

This example illustrates that down-regulation by siRNAs of several key MEF-specific genes encoding proteins with catalytic or regulatory functions, including WISP1, PRRX1, HMGA2, NFIX, PRKG2, COX2, and TGFβ3, greatly increased reprogramming efficiency. Screening results showed that: (a) the non-steroidal anti-inflammatory drug (NSAID) nabumetone acts as a COX2 inhibitor to enhance reprogramming; (b) the anti-cancer drug OHTM can replace Sox2 during reprogramming by inducing endogenous Sox2 expression; and (c) nabumetone can replace c-Myc or Sox2 in reprogramming without compromising self-renewal and pluripotency of derived iPS cells.

The following materials and experimental methods were utilized.

Mouse Embryonic Fibroblast (MEF) Derivation.

Oct4-EGFP MEFs were derived from the mouse strain B6; 129S4-Pou5f1$^{tm2(EGFP)Jae}$/J (The Jackson Laboratory, Bar Harbor, Me., USA, on the world wide web at jax.org/; stock #008214) following the protocol on the WiCell Research Institute, Madison, Wis., USA, on the world wide web at wicell.org/website. In brief, embryonic day 13.5 (E13.5) embryos were collected from timemated pregnant female mice and then tested for microbial contamination. Oct4-EGFP MEFs were maintained in MEF complete medium (Dulbecco's modified Eagle's medium [For DMEM or culture medium & materials: Gibco Cell Culture, Carlsbad, Calif., USA, on the world wide web at invitrogen.com/gibco] with 10% fetal bovine serum (FBS), nonessential amino acids, L-glutamine, and no sodium pyruvate). Cells passaged fewer than five times were used for induced reprogramming.

Reprogramming by Retrovirus-Mediated Transduction of Factors.

Reprogramming was conducted as described in Takahashi et al. (Cell 126: 663-676 (2006)). In brief, $4 \times 10^4$ Oct4-EGFP MEF were transduced with pMX retroviruses for ectopic expression of Oct4, Sox2, Klf4, and c-Myc (Addgene). Three days later, cells were fed ES medium (DMEM with 15% ES-screened FBS, nonessential amino acids, L-glutamine, monothioglycerol, and 1000 U/ml leukemia inhibitory factor (LIF)) and the media was changed every other day. Reprogrammed (EGFP+) cells were identified and scored by fluorescence microscopy two to three weeks post transduction, unless otherwise stated. To derive iPSCs, EGFP+ colonies were manually picked under a stereomicroscope (Leica Microsystems). In the case of small molecule treatment, indicated small molecules were applied to reprogramming cells on day four post-transduction and fresh medium was added every other day for at least two weeks or until EGFP+ colonies appeared.

siRNA Transfection.

Specific siRNAs were purchased from Dharmacon. Approximately $4 \times 10^4$ Oct4-EGFP MEFs were transfected with lipofectamine/siRNAs complexes according to the manufacturer's instruction (Invitrogen). After three to five hours, the transfection reagent was discarded and MEF complete medium was added for culturing. Gene knockdown efficiency was evaluated by semi-quantitative real time RT-PCR. GAPDH served as an internal control to normalize mRNA expression signals.

For reprogramming, retrovirus expressing reprogramming factors (Oct4, Sox2, Klf4, and c-Myc) were added and the medium was then changed to complete medium next day. For overexpression of COX2 transgene, retroviruses expressing COX2 were added 1 day after OSKM transduction. siRNAs were introduced at day 5 post-transduction.

In Vitro Differentiation and Teratoma Formation Assay.

For in vitro differentiation, iPS cells were dissociated by trypsin/EDTA and resuspended in embryoid body (EB) medium (DMEM with 15% FBS, nonessential amino acid, L-glutamine) to final concentration at $5 \times 10^4$ cells/ml. To induce EB formation, 1000 iPS cells in 20 microliter were cultured in hanging drops on inverted Petri dish lids. Three to five days after EB formation, EBs were collected and transferred to 0.1% gelatin-coated E-well plates at a density of ~10 EBs per well. Two weeks later, beating cardiomyocytes (mesoderm) were identified microscopically. Cells derived from endoderm and ectoderm were identified by α-fetoprotein (R&D; Cat#MAB1368) and neuron-specific βIII tubulin (abcam; Cat#ab7751) antibodies, respectively.

To assay teratoma formation, $1.5 \times 10^6$ iPS cells were trypsinized and resuspended in 150 ul of culture medium and injected subcutaneously into the dorsal hind legs of athymic nude mice anesthetized with avertin. Three weeks later, mice were sacrificed to collect teratomas. Tumor masses were fixed, dissected and analyzed in the Sanford-Burnham Medical Institute Cell Imaging-Histology Core Facility.

Immunofluorescence and Alkaline Phosphatase (AP) Staining.

iPS cells were seeded and cultured on 0.1% gelatin-coated 6-well plates. Four days later, cells were fixed with 4% paraformadehyde (Electron Microscopy Sciences; Cat#15710-S). For immunofluorescence, fixed cells were permeabilized with 0.1% Triton X-100 in PBS and blocked with 5% BSA in PBS. SSEA-1 (R&D; Cat#MAB2155), Sox2 (R&D; Cat#MAB2018), and Nanog (R&D; Cat#AF2729) antibodies were used to detect ES markers. Nuclei were visualized by Hoechst 33342 (Invitrogen) staining. For AP staining, fixed cells were treated with alkaline phosphatase substrate following the manufacturer's instruction (Vector Laboratories; Cat#SK-5100).

Microarray Analysis.

Total RNAs were isolated from indicated cells using TRIZOL™ reagent (Invitrogen). Gene expression was detected and normalized in the Sanford-Burnham Medical institute HT screening and genomics core facilities. Heat maps were created using MultiExperiment View™ (available on the world wide web at tm4.org). Scatter plots were created using Excel®.

Meta-Analysis for Small Molecule Candidates.

Select individual MEF or MES (FIG. 1A) genes served as queries to perform searches using the NextBio engine. The compounds identified were analyzed for specific activities, such as down-regulation of the PTGS2 gene by nabumetone. Finally, seventeen molecules (Table 2) were selected as potent inducers of MES genes or inhibitors of MEF genes, as predicted by NextBio meta-analysis.

Silencing MEF-specific genes encoding catalytic or regulatory factors enhance iPSC generation.

To determine quantitatively which genes are specifically expressed in MEF and MES cells, mRNA a microarray analysis was conducted to examine mRNA expression profiles in both cell types. The study focused on MEF-specific genes encoding catalytically active or regulatory proteins based on their important roles in cellular function, and selected WISP1, PRRX1, HMGA2, NFIX, PRKG2, COX2, TGFB3, LYZS, and 6720477E09RIK (FIG. 1A) for further investigation. These genes are highly expressed in MEF but not MES (FIG. 1A) and play key roles in various biological functions (Table 1).

FIG. 1A is a heat map representing mRNA microarray analysis of mouse ES cells (MES) and MEFs. Total RNA isolated from MEFs and MES cells was used for mRNA microarray analysis. The expression intensity of each gene is shown by colorimeter. Key genes encoding catalytic proteins from MEFs or self-renewal factors from MES cells were selected for further investigation.

It was hypothesized that these factors may negatively regulate reprogramming from an MEF to an ESC-like stage by securing identities of fibroblasts and that down-regulation of these genes might enhance the reprogramming process. To test this hypothesis, the effect of knockdown of these genes was examined in Oct4-EGFP MEFs by specific siRNAs. Most genes were knocked down by at least 80% in siRNA-transfected Oct4-EGFP MEFs (FIG. 1B), and that down-regulation persisted for at least five days post-transfection (data not shown).

FIG. 1B shows efficient silencing of MEF-specific genes by siRNAs. MEFs were transfected with siRNAs targeting indicated genes. Cells were harvested ~24 hours post transfection for real time qRT-PCR analysis. Non-targeting (NT) siRNA served as control. Error bars represent standard deviations of six independent experiments.

Since the duration of down-regulation was sufficient to exert an impact on reprogramming, the four reprogramming factors (OSKM: Oct4, Sox2, Klf4, and c-Myc) were introduced into Oct4-EGFP MEFs followed by siRNA transfection five days later (FIGS. 1B and 1C). Two weeks later, mature reprogrammed iPS cells were identified based on GFP-positivity and counted by fluorescence microscopy. Down-regulation of most of the MEF-specific genes encoding catalytic or regulatory factors greatly enhanced reprogramming efficiency by 2 to 6-fold (FIG. 1C) compared with non-targeting (NT) control.

FIG. 1C shows down-regulation of MEF-specific genes significantly improves iPS cell reprogramming. Oct4-EGFP MEFs were transduced with OSKM and five days later transfected with siRNAs targeting indicated genes. Mature reprogrammed iPCS cells were identified as GFP+ colonies and counted by fluorescence microscopy at day 14~16. Error bars represent standard deviations of three independent experiments. * p value <0.05; ** p value <0.005.

The genes exhibiting barrier effects on reprogramming play distinct roles in cellular functions, such as signaling molecules (WISP1 and TGFB3), transcriptional regulators (PRRX1, HMGA2, NFIX, and 6720477E09RIK), and catalytic enzymes (COX2 and PRKG2) (Table 1 below).

TABLE 1

Genes Exhibiting Barrier Effects on Reprogramming.

| Common Name | Reference Sequence | Function Summary* |
|---|---|---|
| WISP1 | NM_018865 | This gene encodes a member of the WNT1 inducible signaling pathway (WISP) protein subfamily, which belongs to the connective tissue growth factor (CTGF) family. WNT1 is a member of a family of cysteine-rich, glycosylated signaling proteins that mediate diverse developmental processes. The CTGF family members are characterized by four conserved cysteine-rich domains: insulin-like growth factor-binding domain, von Willebrand factor type C module, thrombospondin domain and C-terminal cystine knot-like domain. This gene may be downstream in the WNT1 signaling pathway that is relevant to malignant transformation. It is expressed at a high level in fibroblast cells, and overexpressed in colon tumors. The encoded protein binds to decorin and biglycan, two members of a family of small leucine-rich proteoglycans present in the extracellular matrix of connective tissue, and possibly prevents the inhibitory activity of decorin and biglycan in tumor cell proliferation. It also attenuates p53-mediated apoptosis in response to DNA damage through activation of the Akt kinase. It is 83% identical to the mouse protein at the amino acid level. Alternative splicing of this gene generates 2 transcript variants. |
| PRRX1 | NM_011127 | The DNA-associated protein encoded by this gene is a member of the paired family of homeobox proteins localized to the nucleus. The protein functions as a transcription co-activator, enhancing the DNA-binding activity of serum response factor, a protein required for the induction of genes by growth and differentiation factors. The protein regulates muscle creatine kinase, indicating a role in the establishment of diverse mesodermal muscle types. Alternative splicing yields two isoforms that differ in abundance and expression patterns. |
| HMGA2 | NM_010441 | This gene encodes a protein that belongs to the non-histone chromosomal high mobility group (HMG) protein family. HMG proteins function as architectural factors and are essential components of the enhancesome. This protein contains structural DNA-binding domains and may act as a transcriptional regulating factor. Identification of the deletion, amplification, and rearrangement of this gene that are associated with myxoid liposarcoma suggests a role in adipogenesis and mesenchymal differentiation. A gene knock out study of the mouse counterpart demonstrated that this gene is involved in diet-induced obesity. Alternate transcriptional splice variants, encoding different isoforms, have been characterized. |
| NFIX | NM_001081982 | ¶Recognizes and binds the palindromic sequence 5'-TTGGCNNNNNGCCAA-3' (SEQ ID NO: 1) present in viral and cellular promoters and in the origin of replication of adenovirus type 2. These proteins are individually capable of activating transcription and replication. |

TABLE 1-continued

Genes Exhibiting Barrier Effects on Reprogramming.

| Common Name | Reference Sequence | Function Summary* |
|---|---|---|
| PRKG2 | NM_008926 | §AMP-activated protein kinase (AMPK) is a heterodimeric protein serine/threonine kinase that is composed of alpha-(catalytic) and beta/gamma-(regulatory) subunits. AMPK acts as a sensor of the energy status of cells and ensures survival at times of metabolic stress. AMPK phosphorylates many metabolic enzymes to stimulate catabolic pathways, such as ketogenesis, and inhibit anabolic pathways, such as protein synthesis. The long-term activation of AMPK increases the capacity of cells to produce ATP. AMPK is regulated by phosphorylation at the Thr-172 residue of the alpha-subunit by AMPKK and by phosphorylation by calmodulin-dependent protein kinase kinase-beta (CamKKbeta). In addition, the ratio of AMP:ATP mediates allosteric activation of the enzyme. AMPK is found throughout the body with high concentrations in metabolically active tissues such as the skeletal muscles and liver. |
| COX2 (PTGS2) | NM_011198 | Prostaglandin-endoperoxide synthase (PTGS), also known as cyclooxygenase, is the key enzyme in prostaglandin biosynthesis, and acts both as a dioxygenase and as a peroxidase. There are two isozymes of PTGS: a constitutive PTGS1 and an inducible PTGS2, which differ in their regulation of expression and tissue distribution. This gene encodes the inducible isozyme. It is regulated by specific stimulatory events, suggesting that it is responsible for the prostanoid biosynthesis involved in inflammation and mitogenesis. |
| TGFB3 | NM_009368 | This gene encodes a member of the TGF-beta family of proteins. The encoded protein is secreted and is involved in embryogenesis and cell differentiation. Defects in this gene are a cause of familial arrhythmogenic right ventricular dysplasia 1. |
| LZYS | NM_017372 | C-type lysozyme (1,4-beta-N-acetylmuramidase, LYZ) and alpha-lactalbumin (lactose synthase B protein, LA). They have a close evolutionary relationship and similar tertiary structure, however, functionally they are quite different. Lysozymes have primarily bacteriolytic function; hydrolysis of peptidoglycan of prokaryotic cell walls and transglycosylation. LA is a calcium-binding metalloprotein that is expressed exclusively in the mammary gland during lactation. LA is the regulatory subunit of the enzyme lactose synthase. The association of LA with the catalytic component of lactose synthase, galactosyltransferase, alters the acceptor substrate specificity of this glycosyltransferase, facilitating biosynthesis of lactose. |
| 6720477E09RIK | NM_001172121 | This gene encodes an RNA-binding protein that belongs to the c-myc gene single-strand binding protein family. These proteins are characterized by the presence of two sets of ribonucleoprotein consensus sequence (RNP-CS) that contain conserved motifs, RNP1 and RNP2, originally described in RNA binding proteins, and required for DNA binding. These proteins have been implicated in such diverse functions as DNA replication, gene transcription, cell cycle progression and apoptosis. The encoded protein was isolated by virtue of its binding to an upstream element of the alpha2(I) collagen promoter. The observation that this protein localizes mostly in the cytoplasm suggests that it may be involved in a cytoplasmic function such as controlling RNA metabolism, rather than transcription. Multiple alternatively spliced transcript variants encoding different isoforms have been found for this gene. |

*Information is collected through NCBI RefSeq, unless otherwise stated.
¶Information is collected from Protein Knowledgebase in UniProt.
§Information is collected from TOCRIS bioscience (on the world wide web at tocris.com).

Most of these identified genes are novel to reprogramming, except TGFβ pathway which has previously been reported to act as a roadblock during reprogramming. Interestingly, LYZS depletion showed reduction of iPS cells (FIG. 1C).

Figure 5:
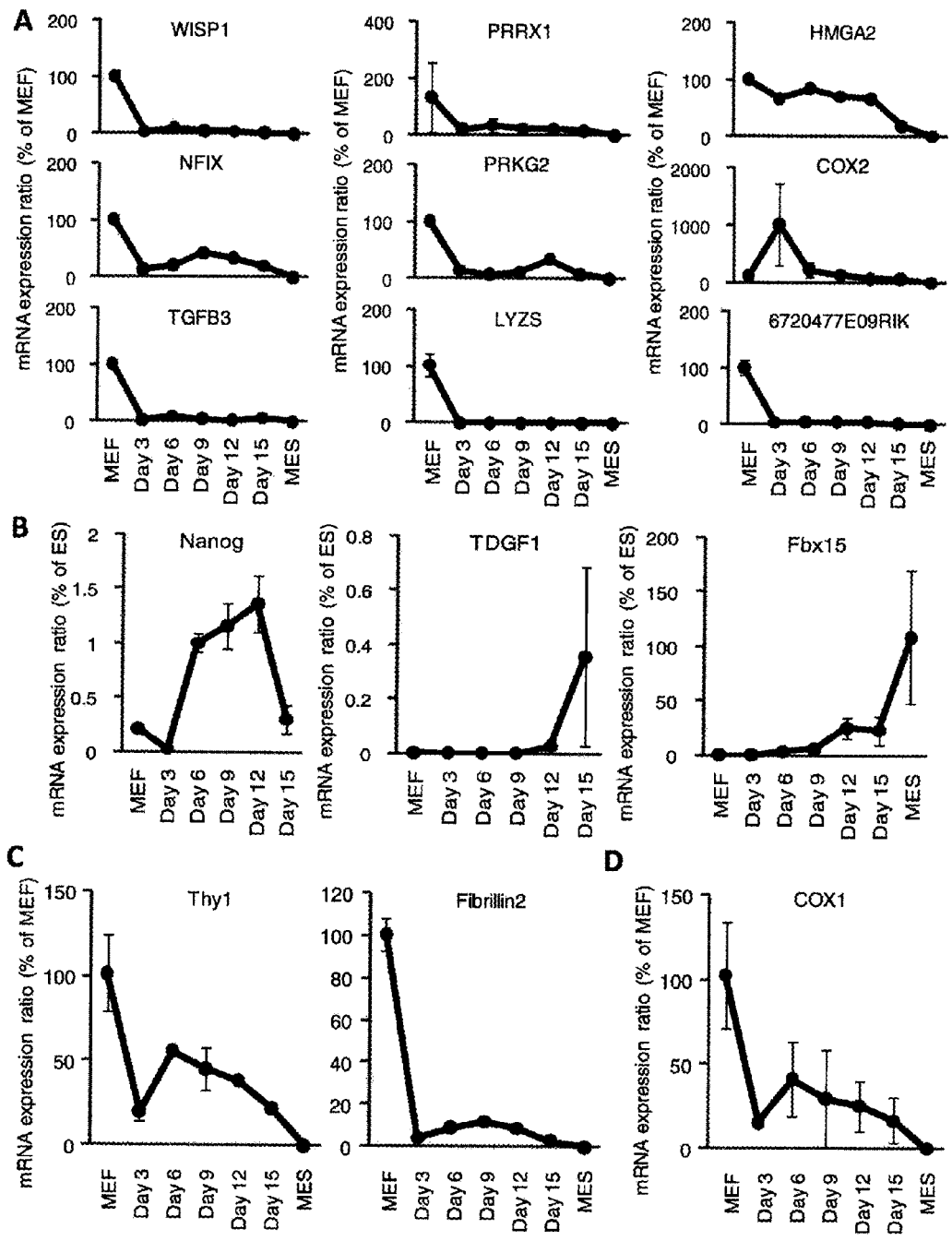
FIG. 5, is a series of graphical representations.

In addition, quantitative expression was examined of a selected set of MEF-specific genes during reprogramming process (FIG. 5). All the genes analyzed decreased upon induction of reprogramming, except COX2, which increased at the early-stage of reprogramming followed by a dramatic decrease (FIG. 5A). Expression levels of all these genes were diminished in late stage of reprogramming (day 12 or day 15) as in ESCs. These gene expression patterns indicate that MEF-specific molecular network will be disrupted by 4F to achieve the cell fate transitions during reprogramming. In summary, these results support the idea that MEF-specific catalytic or regulatory proteins can negatively regulate reprogramming and also suggest that it is critical to modulate diverse biological functions during transition of cell identities such as MEFs to iPSCs.

FIG. 5A shows selected MEF-specific genes dramatically decrease during reprogramming, except COX2. As discussed above, real-time qRT-PCR analysis of a selected set of genes during reprogramming. Oct4-MEFs were transduced with OSKM to induce reprogramming. Transduced cells were collected at various time points for isolating total RNAs and real-time qRT-PCR analysis. GAPDH mRNA expression level served as internal control. Expression level of target genes was normalized to those in MEFs. MES served as control. Error bars represent standard deviations of at least two independent experiments.

FIG. 5B shows MES-specific genes were induced during reprogramming. Experiments were performed as described in A and which served as indicators of reprogramming progress. Error bars represent standard deviations of at least two independent experiments.

FIG. 5C shows differentiated markers Thy1 and Fibrillin2 were diminished during reprogramming. These data were created as described in FIG. 5A and which served as indicators of de-differentiation progress. Error bars represent standard deviations of at least two independent experiments.

FIG. 5D shows COX1 decreased dramatically upon induction of reprogramming. These data were created as described in FIG. 5A. Error bars represent standard deviations of at least two independent experiments.

The NSAID Nabutone Enhances iPS Cell Generation.

Next, a genomics database drug discovery strategy was developed to identify small molecules that enhance reprogramming. To shorten the list without extensive shot-gun screening, candidate molecules that potentially either antagonized MEF-specific genes or upregulated MES-specific/reprogramming genes were focused on (FIG. 1A). To do so, computational screening by utilizing NextBio (nextbio.com) data-mining tools to collect information from public data sources was conducted as in Kupershmidt et al. (*PLoS* One 5 (2010)). Using highly enriched genes in either MES or MEF (FIG. 1A) as queries, 17 molecules (Table 2) were acquired that either negatively regulated MEF genes or positively affected MESC genes from various in vitro and in vivo studies deposited in public data bases.

TABLE 2

Molecules that either negatively regulate MEF genes or positively affect MES genes.

| ID | Molecules | CAS # | Predicted targets |
|----|-----------|-------|-------------------|
| 1 | Nickel sulfate hexahydrate (NiSO$_4$) | 10101-97-0 | WISP1, PRRX1, LYZS |
| 2 | 2,3,7,8-tetrachlorodibenzo-p-dioxin | 1746-01-6 | TGF-β3 |
| 3 | Nabumetone | 42924-53-8 | COX2 |
| 4 | 4-hydroxytamoxifen (OHTM) | 68047-06-3 | Sox2 |
| 5 | Moclobemide | 71320-77-9 | Nanog |
| 6 | Lectin | | DPPA5 |
| 7 | Corynanthine hydrochloride | 66634-44-4 | TDGF1 |
| 8 | TGF-β | | Oct3/4 |
| 9 | Acitretin | 55079-83-9 | Oct3/4 |
| 10 | Retinoic acid p-hydroxyanilide | 65646-68-6 | Oct3/4 |
| 11 | Diacerein | 13739-02-1 | Nanog |
| 12 | Phorbol 12-myristate 13-acetate | 16561-29-8 | Nanog |
| 13 | Progesterone | 57-83-0 | Nanog |
| 14 | Tolazamide | 1156-19-0 | Nanog |
| 15 | 15-deoxy-$\Delta^{12,\ 14}$-prostaglandin J$_2$ | 89886-60-2 | Klf4 |
| 16 | (−)-Norepinephrine | 51-41-2 | c-Myc |
| 17 | β-estradiol | 50-28-2 | c-Myc |

All 17 molecules were tested by examining alkaline phosphatase (AP)+ colony formation during reprogramming while these molecules were applied. Molecules not showing adverse effect on AP+ colony formation (data not shown) were picked for further study. To that end, 6 molecules were picked including nabumetone, 4-hydroxytamoxifen (OHTM), corynanthine, moclobemide, NiSO$_4$, and lectin—for further analysis (FIG. 2A). To evaluate their effect on induction of mature GFP+ iPS cells, OSKM-transduced Oct4-EGFP MEFs were treated four days after transduction with each of these factors separately. Among the six, the NSAID prostaglandin-endoperoxide synthase (PTGS) and the cyclooxygenase (COX) inhibitor nabumetone greatly increased the number of reprogrammed colonies by at least 2.8-fold (FIG. 2B) compared with DMSO controls, while lectin showed minor but consistent improvement on iPSC formation.

As MEFs mainly express the COX2 isozyme (verified by quantitative RT-PCR [qRT-PCR], data not shown) it was proposed that COX2 is the primary nabumetone target during reprogramming. To test that idea, COX2 was knocked down in Oct4-EGFP MEFs by siRNA with or without nabumetone during reprogramming with OSKM. In the presence of control siRNA (siNT), nabumetone alone enhanced reprogramming efficiency by more than 6-fold (FIG. 2C) compared with DMSO treatment. Transduction of cells with COX2 siRNA increased the number of GFP+ iPS cell colonies by over 5-fold compared with cells transduced with siNT control (FIG. 2C). However, no further enhancement of reprogramming efficiency in the presence of both siCOX2 and nabumetone (FIG. 2C) was observed, likely due to the maximal COX2 silencing effects by siRNA.

FIG. 2B shows that nabumetone significantly boosts OSKM-induced reprogramming while lectin showed minor but consistent increase as well. Oct4-EGFP MEFs were transduced with OSKM and four days later treated with individual small molecules for at least 10 days. GFP+ colonies were identified as described in FIG. 1. Error bars represent standard deviations of three independent experiments. * p value <0.05; ** p value <0.005.

FIG. 2C shows that nabumetone improves reprogramming through blocking COX2. Oct4-EGFP MEFs were transduced with OSKM. Four days later, cells were treated with nabumetone or DMSO. The next day, cells were transfected with various siRNAs as indicated. GFP+ colonies were identified as described in FIG. 1 at day 12~14. Error bars represent standard deviations of six independent experiments. * p value <0.05;  p value <0.005; * p value <0.0005. siNT serves as control.

Figure 6:
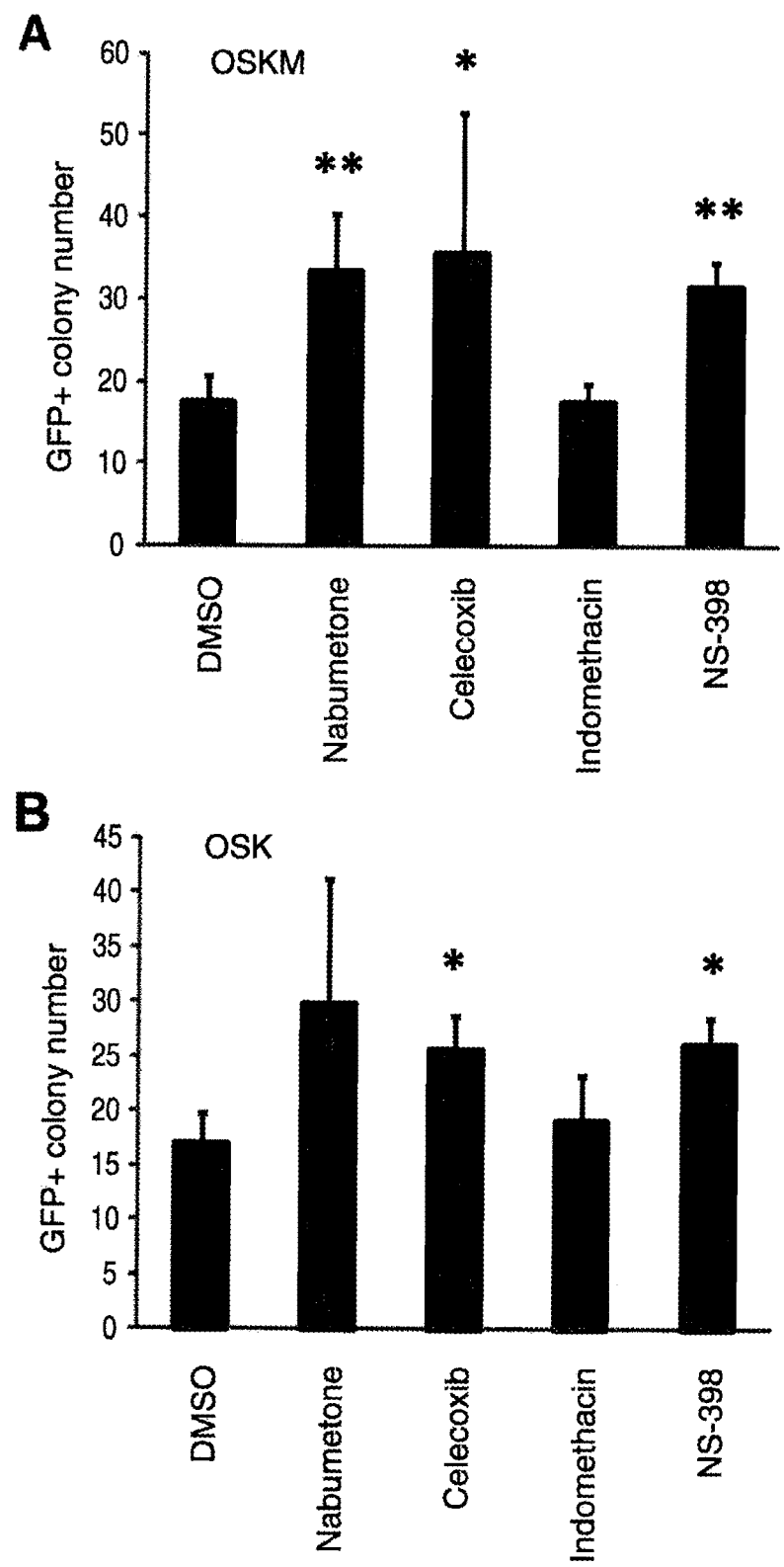
FIG. 6 is a series of graphical representations.

To determine whether the COX2 is the main target instead of COX1, which is constitutively expressed in various tissues, selective inhibitors targeting either COX1 or COX2 during reprogramming with OSKM or OSK were applied. Interestingly, only the selective COX2 inhibitors, celecoxib, and NS-398 showed similar effects on iPSC generation as nabumetone with OSKM or OSK pluripotency factors (FIG. 6). On the other hand, selective COX1 inhibitor, indomethacin, showed no effect to boost reprogramming with OSKM or OSK (FIG. 6), although COX1 greatly decreased upon induction of reprogramming (FIG. 5D).

As discussed, FIG. 6 shows specific COX2 inhibitors significantly enhance OSKM and OSK reprogramming. Oct4-MEFs were transduced with OSKM (FIG. 6A) or OSK (FIG. 6B) to induce reprogramming. Small molecules were applied at day 4~5 post transduction. EGFP+ colony number was scored under fluorescent microscopy at two weeks post transduction. Error bars represent standard deviations of at least three independent experiments. * P value <0.05; ** P value <0.005.

To further investigate the role of COX2 in reprogramming, COX2 along with OSKM were cloned and overexpressed during reprogramming. Results showed that overexpression of COX2 compromised reprogramming with OSKM pluripotency factors (FIG. 7).

Figure 7:
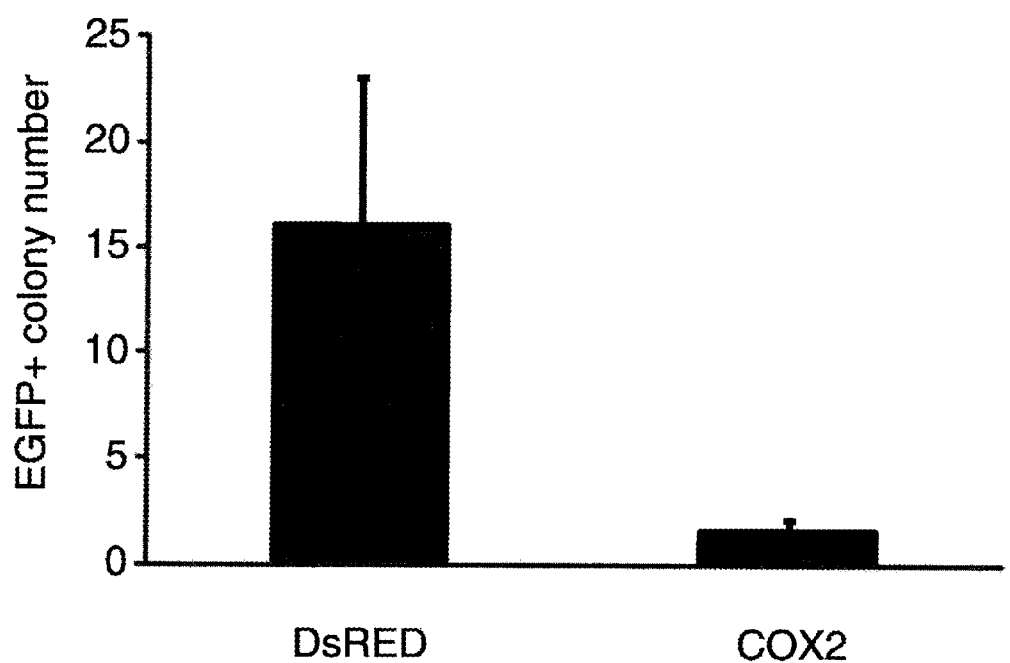
FIG. 7 is a graphical representation plotting EGFP+ colony number. Oct4-MEFs were transduced with OSKM to induce reprogramming. Retroviruses overexpressing COX2 transgene were transduced one-day post OSKM transduction. EGFP+ colony number was scored under fluorescent microscopy at two weeks post transduction. Error bars represent standard deviations of at least three independent experiments. DsRED transgene served as control.

FIG. 7 shows overexpression of COX2 compromised OSKM reprogramming. Oct4-MEFs were transduced with OSKM to induce reprogramming. Retroviruses overexpressing COX2 transgene were transduced one-day post OSKM transduction. EGFP+ colony number was scored under fluorescent microscopy at two weeks post transduction. Error bars represent standard deviations of at least three independent experiments. DsRED transgene served as control.

Overall, these results support the notion that COX2 is a barrier for reprogramming and that nabumetone enhances reprogramming by mainly blocking COX2 activity.

Nabumetone can Generate iPSCs in the Absence of c-Myc.

To further analyze nabumetone reprogramming potential, it was contemplated whether nabumetone can replace the proto-oncogene c-Myc, which may greatly increase tumorigenesis in vivo. Oct4-EGFP MEFs were reprogrammed using either OSKM or OSK without c-Myc, and induced cells were treated with nabumetone or DMSO four days later. Nabumetone treatment significantly enhanced reprogramming by OSK by ~2.5-fold as assessed at day 21 (FIG. 3A) compared with control OSK+DMSO. This data suggests that nabumetone not only improves OSKM reprogramming, likely by blocking COX2, but can partially replace c-Myc function in the process.

FIG. 3A shows that nabumetone replaces c-Myc during reprogramming. Oct4-EGFP MEFs were transduced with OSK without c-Myc and four days later treated with nabumetone or DMSO for two weeks. Cells transduced with OSKM are shown for comparison. GFP+ colonies were identified as described in FIG. 1 at day 21. Error bars represent standard deviations of two independent experiments. * p value <0.05.

OHTM and Nabumetone can Produce iPSCs Without Sox2.

Whether the small molecules identified in the analysis can replace the need for other reprogramming factors was next posed. To do so a pool of the six candidate molecules was tested for their ability to replace any single reprogramming factor. Strikingly, the pool replaced Sox2 during reprogramming of Oct4-EGFP MEF with OKM and significantly increased reprogramming efficiency by more than 10-fold (FIG. 3B) compared with controls. To determine which molecule(s) exerted that effect, each of the six small molecules in OKM reprogramming protocols were individually tested. It was determined that the anti-cancer drug OHTM significantly improved OKM-induced reprogramming, while OKM+ DMSO did not produce any mature iPS colonies (FIG. 3C). Similarly, nabumetone significantly improved OKM-induced reprogramming, which showed comparable effect with OHTM (FIG. 3D). Overall, these results indicate that either OHTM or nabumetone can replace Sox2 function to generate iPSCs.

FIG. 3B shows a pool of six molecules with OKM reprograms MEFs to iPSCs. Oct4-EGFP MEFs were transduced with OKM and treated with pool of 6 molecules, including $NiSO_4$, nabumetone, OHTM, moclobemide, lectin, and corynanthine, at day 4 for at least 10 days. GFP+ colonies were identified and counted as described in FIG. 1 at day 14. Error bars represent standard deviations of six independent experiments. *** p value <0.0005.

FIG. 3C shows that OHTM plus OKM reprograms MEFs to iPSCs. Oct4-EGFP MEFs were transduced with OKM and four days later treated with 1.25 uM OHTM at least 10 days. GFP+ colonies were counted as described in FIG. 1 at day 15~21. Error bars represent standard deviations of four independent experiments. ** p value <0.005.

FIG. 3D shows that nabumetone plus OKM reprograms MEFs to iPSCs. Oct4-EGFP MEFs were transduced with OKM and four days later treated with 2.18 uM nabumetone (Nabu) for at least 10 days. GFP+ colonies were counted as described in FIG. 1 at day 17~21. Error bars represent standard deviations of three independent experiments. ** p value <0.005.

OHTM Increases Endogenous Sox2 Expression During OKM Reprogramming.

To understand the molecular mechanism underlying OHTM's effect on reprogramming, the question of whether OHTM induces endogenous Sox2 expression was posed. To do so, OHTM or control DMSO was applied to Oct4-EGFP MEF four days after transduction with OKM. Cells were harvested at indicated time points for total RNA isolation and real time qRT-PCR analysis (FIG. 3E). Strikingly, endogenous Sox2 mRNA was significantly induced by 220% by OHTM in OKM-transduced cells at day 12 and by 400% at day 16 compared with OKM+DMSO controls, indicating that OHTM enhances reprogramming, at least partially, by inducing Sox2 expression. However, the direct targets of OHTM to affect Sox2 expression were not clear.

FIG. 3E shows that Sox2 expression is significantly induced by OHTM during OKM-induced reprogramming. Oct4-EGFP MEFs were transduced with OKM and treated with OHTM four days later. Cells were harvested at indicated days (D) for real time RT-PCR analysis. β actin expression serves as an internal control. Error bars represent standard deviation of 2~3 independent experiments. * p value <0.05.

OKM+OHTM or OKM+Nabumetone iPS Cells Attain ES Identity and Pluripotency.

To verify whether iPSCs derived with OKM in the presence of pooled or individual molecules attain self-renewal and pluripotency, iPSCs for these properties were analyzed. Genomic DNAs were isolated from OKM plus the six-molecule pool (OKM+6), OKM+OHTM, or OKM+nabumetone iPSCs to verify transgene integration by PCR analysis. OKM iPSC clones showed no Sox2 transgene integration (data not shown), demonstrating OKM iPSCs could be derived with pool of six molecules, OHTM or nabumetone alone in the absence of Sox2 transgene.

Figure 4:
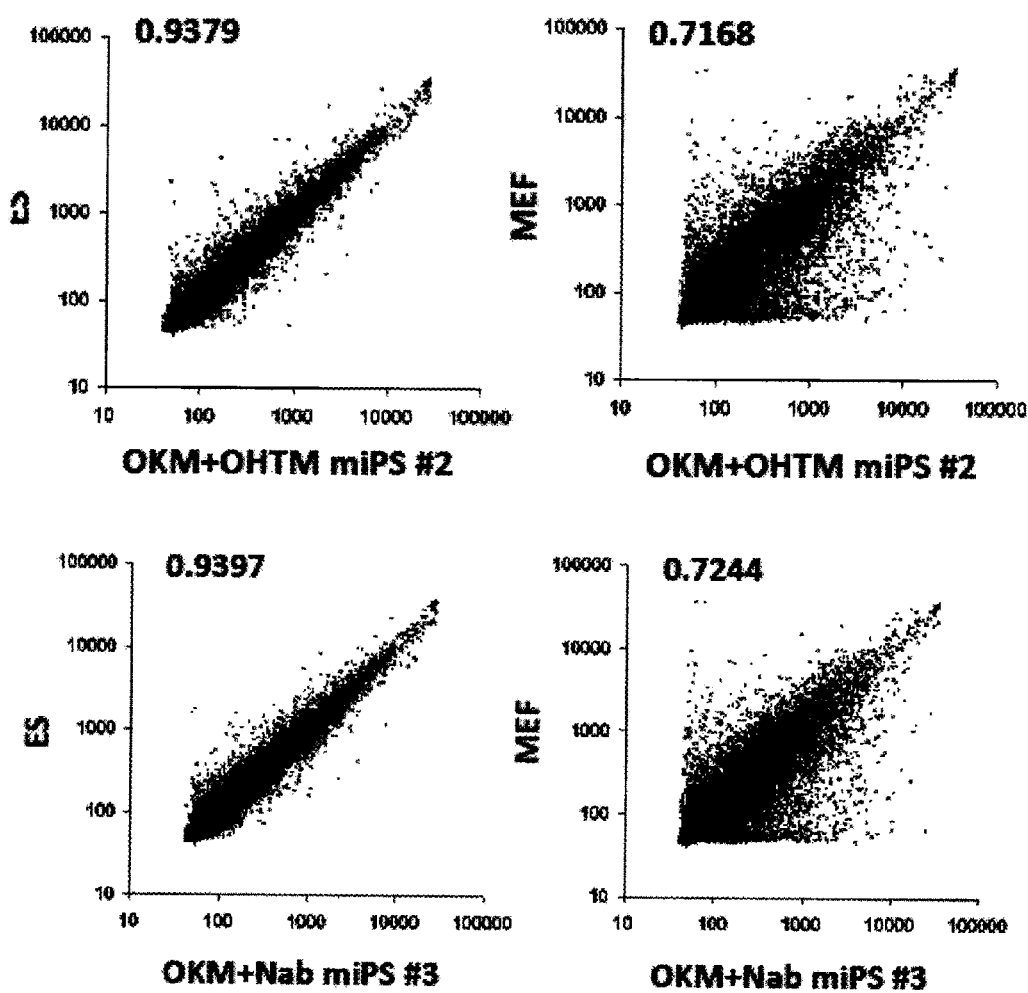
FIG. 4 is a series of graphical representations. A series of scatter plots is depicted of transcriptome comparison of iPS clones with ES or MEF cells. Total RNA was isolated from indicated iPS cells and subjected to mRNA microarray analysis. $R^2$ values are shown at the top of each panel.

When OKM iPSCs were cultured for at least 1 month (more than 10 passages) and fixed them for immunostaining, OKMþ 6 and OKM+nabumetone iPSCs exhibited ESC-like dome shape morphology with a clear boundary (data not shown), and they highly expressed endogenous Oct3/4 (EGFP) and Nanog (data not shown), indicating establishment of ESC-like transcriptional networks. OKM+6 iPSCs expressed SSEA1 (data not shown), and OKM+nabumetone iPSCs also acquired the stem cell marker AP (data not shown). Importantly, endogenous Sox2 expression was activated in OKM+nabumetone iPSCs (data not shown), suggesting that a full self-renewal circuit was restored. To confirm restoration of an ESC-like transcriptome, mRNA expression profiles were examined of OKM+OHTM and OKM+nabumetone iPSCs by microarray analysis. Representative clones from OKM+OHTM iPSCs showed a high degree of similarity with ESCs, but not MEFs (FIG. 4), as did OKM+nabumetone iPS clones (FIG. 4).

To determine whether OKM plus small molecule-derived iPSCs show pluripotency comparable with ESCs, in vitro differentiation capacity was first tested. OKM+6 iPSCs were induced to form EBs for 2 weeks and then fixed for immunostaining. After 2 weeks of in vitro differentiation, cell types typical of all three germ layers were observed (data not shown). To further assess differentiation potential, OKM+OHTM and OKM+nabumetone iPSCs were injected into nude mice and allowed to differentiate into various tissues. Teratomas, which were observed 3 weeks postinjection, were subjected to histopathological analysis. Tissues originating from all three germ layers were generated (data not shown), confirming that iPSCs obtained pluripotency. To vigorously test pluripotency of OKM iPSCs, OKM+nabumetone iPSCs were injected into E3.5 blastocysts to create chimera. Contributions of OKM+nabumetone iPSCs to chimera mice were accessed by black coat color at day 17 after birth. OKM+nabumetone iPSCs contribution up to 50% (data not shown) was obtained. Next the germline transmission capability of OKM+nabumetone iPSCs was examined. By analyzing E13.5 embryos after injecting OKM+nabumetone iPSCs into blastocysts, strong Oct4-EGFP expression in genital ridge (data not shown) was found, showing germline contribution of OKM+nabumetone iPSCs.

In summary, the data demonstrate that small molecule with OKM derived iPSCs do attain ESC identity and pluripotency.

Based on knowledge of the reprogramming steps, is was hypothesized that overcoming an MEF-specific network is the first step in the process. It was observed that specific siRNA-mediated knockdown of MEF genes encoding catalytic or regulatory proteins, including WISP1, PRRX1, HMGA2, NFIX, PRKG2, COX2, 6720477E09RIK, and TGFβ3, significantly enhanced reprogramming (FIG. 1). To accelerate screening of small molecules, a computational screening method was employed using the NextBio datamining framework (Kupershmidt et al., Id.) and identified six molecules (FIG. 2), including nabumetone, OHTM, corynanthine, moclobemide, $NiSO_4$, and lectin, which function together to reprogram MEFs without Sox2 (FIG. 3). One of those factors alone, OHTM, could partially replace the Sox2 transgene during reprogramming by inducing endogenous Sox2 expression (FIG. 3). It was further shown that nabumetone enhances reprogramming by inhibiting COX2 activity (FIG. 3). Finally, it was shown that nabumetone also promotes reprogramming by partially replacing c-Myc or Sox2 function without compromising self-renewal and pluripotency of small molecule-derived iPS cells.

Nabumetone is a non-steroidal anti-inflammatory drug (NSAID) known to be used clinically to primarily treat pain and inflammation associated with osteoarthritis (OA) or rheumatoid arthritis (RA). Nabumetone exerts anti-inflammatory activity by inhibiting COX2 function through its metabolite 6-methoxy-2-naphthylacetic acid (6-MNA). Moreover, it is reported that NSAIDs compromise tumor growth in clinical cases and experimental models of cancer, and also that two isoforms cyclooxygenase-1 and -2 function in a variety of pathophysiological processes, such as modulating apoptosis, angiogenesis, invasion, and carcinogenesis. Reported preliminary in vitro and in vivo studies have shown that following COX inhibition, signals regulating cell proliferation and apoptosis networks, including EGFR, KRas, PI3K, JAK1, STAT3, c-jun, PCNA, TGFβ3, BAX, TUNEL, Bcl-2, c-jun, p21, p27, p53, and NM23, are widely altered in tumor cell. However, the roles of COX inhibitors in tumorigenesis remains controversial, since COX2 expression has been reported to differ widely in different types of cancer cells. In this study, it was shown that COX2 is highly expressed in MEFs and serves as a barrier to reprogramming.

Tamoxifen is a standard chemotherapy used to treat primary and advanced breast cancer by blocking the estrogen receptor (ER) via its metabolites OHTM and endoxifen. OHTM activity has been addressed primarily through its effect on the ER. However, detectable levels of ER expression in MEFs was not observed (data not shown). OHTM-induced programmed cell death can reportedly be induced through ER-independent pathways in HeLa cells, suggesting that other factors respond to OHTM. Moreover, 3,4-dihydroxytamoxifen, a more hydroxylated form of OHTM, has been shown to interact with both proteins and DNA, suggesting the possibility of numerous targets in vivo.

Reprogramming of somatic cells to iPSCs by small molecules could facilitate pharmaceutical and medical applications of pluripotent stem cells. A number of studies have identified small molecules that enhance reprogramming by targeting various pathways including TGFb and GSK3. Although iPSCs can be generated in the absence of Sox2, only RepSox has been shown to partially induce Nanog expression in partial iPS cells. This is the first report that Sox2 can be induced by OHTM treatment during reprogramming.

Increasing evidence shows that overcoming the security of somatic cell identity is a critical step initiating the transition from mesenchymal to epithelial status. This step requires large-scale regulation of opposing genes within only few days during the first 8 days of reprogramming, including Cdh1, Epcam, Crb3, Ocln, Snail, Slug, Zeb1, Zeb2, BMP, and TGFβ pathways. Since TGFβ3 has also been implicated herein and TGFβ3 knock-down greatly enhances reprogramming efficiency, these data support the idea that down-regulating MEF regulatory factors is an effective approach to enhance reprogramming. Furthermore, the study confirms that downregulation of MEF genes encoding catalytic factors constitutes some of the earliest steps of reprogramming and that attenuating key somatic genes is critical to enhance reprogramming efficiency.

In summary, mouse ES cells express regulatory genes that differ from those expressed in MEFs. Reasoning that the latter encode factors that maintain MEF function and establish fibroblast identity, they were manipulated using either siRNAs or small molecules in an effort to enhance reprogramming efficiency. This hypothesis-driven approach provides an alternative to shot-gun screening, which should accelerate understanding of the molecular mechanism underlying generation of iPS cells and suggest novel therapeutic methodologies.

Although the invention has been described with reference to the above example, it will be understood that modifications and variations are encompassed within the spirit and scope of the invention. Accordingly, the invention is limited only by the following claims.

What is claimed is:

1. An in vitro method of generating an induced pluripotent stem cell (iPSC) comprising:
   a) contacting a human or mouse fibroblast cell with nuclear reprogramming factors, the nuclear reprogramming factors being OCT4, SOX2, KLF4 and C-MYC, wherein the nuclear reprogramming factors are encoded by one or more polynucleotides; and
   b) contacting the cell of (a) with an agent that inhibits COX-2 expression or activity, wherein the agent is a polynucleotide, and wherein reprogramming efficiency is increased as compared to generation of an iPSC without contacting the cell with the agent, thereby generating an iPS cell.

2. The method of claim 1, wherein the nuclear reprogramming factors are contained in one or more recombinant vectors introduced into the cell.

3. The method of claim 2, wherein the nuclear reprogramming factors further comprise SALL4, NANOG, L1N28 or a combination thereof.

4. The method of claim 1, wherein the cell is contacted with the nuclear reprogramming factors prior to, simultaneously with or following contacting with the agent.

5. The method of claim 1, wherein the nuclear reprogramming factors further comprise SALL4, NANOG, LIN28, or a combination thereof.

6. The method of claim 1, wherein the method has a reprogramming efficiency that is increased by at least a factor of 2, 3, 4, 5, 6, 7, 8, 9, 10 or greater as compared to generation of an iPSC without contacting the cell with the agent.

7. An induced pluripotent stem cell (iPSC) produced using the method of claim 1.

8. A population of induced pluripotent stem cells (iPSCs) produced by the method of claim 1.

9. The method of claim 1, wherein the polynucleotide of (b) is an antisense oligonucleotide, chemically modified oligonucleotides, locked nucleic acid (LNA), or DNA.

10. The method of claim 1, wherein the polynucleotide of (b) is RNA.

11. The method of claim 10, wherein the RNA is selected from the group consisting of microRNA, dsRNA, siRNA, stRNA, or shRNA.

12. The method of claim 11, wherein the RNA is siRNA.

* * * * *